United States Patent
Devisetty et al.

(10) Patent No.: US 9,801,380 B2
(45) Date of Patent: Oct. 31, 2017

(54) LOW VOC GIBBERELLIN FORMULATIONS

(71) Applicant: Valent BioSciences Corporation, Libertyville, IL (US)

(72) Inventors: Bala N. Devisetty, Buffalo Grove, IL (US); Johan Daniel Pienaar, Grayslake, IL (US); Robert Fritts, Jr., Clovis, CA (US); Gregory D. Venburg, Deerfield, IL (US)

(73) Assignee: Valent BioSciences LLC, Libertyville, IL (US)

( * ) Notice: Subject to any disclaimer, the term of this patent is extended or adjusted under 35 U.S.C. 154(b) by 22 days.

(21) Appl. No.: 14/573,476

(22) Filed: Dec. 17, 2014

(65) Prior Publication Data

US 2015/0173365 A1    Jun. 25, 2015

Related U.S. Application Data

(60) Provisional application No. 61/918,821, filed on Dec. 20, 2013.

(51) Int. Cl.
| | | |
|---|---|---|
| *A01N 45/00* | (2006.01) | |
| *A01N 25/30* | (2006.01) | |
| *A01N 25/02* | (2006.01) | |
| *A01N 43/12* | (2006.01) | |

(52) U.S. Cl.
CPC ............. *A01N 45/00* (2013.01); *A01N 43/12* (2013.01)

(58) Field of Classification Search
CPC ........ A01N 25/02; A01N 25/30; A01N 43/12; A01N 45/00
USPC ........................................................ 504/297
See application file for complete search history.

(56) References Cited

U.S. PATENT DOCUMENTS

| | | | |
|---|---|---|---|
| 3,778,247 A * | 12/1973 | Pyne ................ | C07D 295/215 504/287 |
| 4,936,901 A | 6/1990 | Surgant, Sr. et al. | |
| 5,163,993 A | 11/1992 | Shafer et al. | |
| 5,622,658 A | 4/1997 | Lloyd et al. | |
| 6,984,609 B2 | 1/2006 | Devisetty et al. | |
| 2003/0008949 A1* | 1/2003 | Devisetty ............... | A01N 25/12 524/56 |
| 2006/0003898 A1 | 1/2006 | Devisetty et al. | |
| 2008/0039322 A1 | 2/2008 | Wang et al. | |
| 2010/0216641 A1 | 8/2010 | Wang et al. | |
| 2012/0220459 A1 | 8/2012 | Wang et al. | |

FOREIGN PATENT DOCUMENTS

| | | |
|---|---|---|
| CN | 102885082 | 1/2013 |
| EP | 0 252 897 | 2/1994 |

OTHER PUBLICATIONS

ISR and Written Opinion in corresponding Application No. PCT/US2014/070835 issued Apr. 7, 2015.
The Dow Chemical Company Material Safety Data Sheet, Carbowax™ Polyethylene Glycol 200. 1-16, Aug. 6, 2002.
Technical Data Sheet, Carbowax(TM) Polyethylene Glycol (PEG) 200, Dow, Form No. 118-01796-1211, available from website URL: http://www.dow.com/webapps/lit/litorder.asp?filepath=polyglycols/pdfs/noreg/118-01796.pdf.

* cited by examiner

*Primary Examiner* — Johann R Richter
*Assistant Examiner* — Courtney Brown
(74) *Attorney, Agent, or Firm* — Wood, Phillips, Katz, Clark & Mortimer

(57) ABSTRACT

The invention relates to low volatile organic chemical gibberellic acid ("$GA_3$"), gibberellin 4 ("$GA_4$"), gibberellin $_{4/7}$ ("$GA_{4/7}$"), or combinations thereof formulations and methods of their use. Specifically, formulations of the present invention are directed toward agricultural formulations including from about 1 to about 10% of at least one gibberellin selected from the group consisting of $GA_3$, $GA_4$, and $GA_{4/7}$, from about 85 to about 99% polyethylene glycol with a molecular weight from about 190 to about 420, and from about 0.1 to about 5% of a non-ionic or anionic surfactant, wherein the formulation does not include isopropyl alcohol, and wherein the percentages are percent by weight of the formulation.

18 Claims, No Drawings

LOW VOC GIBBERELLIN FORMULATIONS

FIELD OF THE INVENTION

The present invention relates to gibberellic acid ("$GA_3$"), gibberellin 4 ("$GA_4$"), or gibberellin 4/7 ("$GA_{4/7}$") formulations containing low amounts of volatile organic chemicals ("VOCs") and methods of their use.

BACKGROUND OF THE INVENTION

Gibberellins are a class of plant growth regulators which are diterpenoid acids. Gibberellins are commercially produced by fermentation of a natural fungus, *Gibber ellafugikuroi*. Gibberellins are marketed under various trade names and are commercially used on a variety of fruit orchards, vegetable crops, row crops, and ornamental crops. The predominantly used gibberellin is $GA_3$.

VOCs contribute to the formation of ground-level ozone, which is harmful to human health and vegetation when present at high enough concentrations. Gibberellin formulations with greater than 25% emission potential, as determined by thermo gravimetric analysis ("TGA"), are considered High-VOC products by CADPR (California Department of Pesticide Regulation). TGA involves heating a pesticide sample in an environmentally controlled chamber while the rate of sample mass loss is measured. CADPR states that the emission potential of a pesticide formulation is determined by taking the mean of three replicate TGA measurements of the pesticide(s) and then subtracting the percent water and the exempt compounds from the measurement. The TGA process is well known by those of skill in the art.

Gibberellin solution formulations of the prior art are disadvantageous in several respects. The formulations are less concentrated due to low solubility of gibberellins, have limited storage stability, and/or contain unacceptable amounts of VOCs.

In order to overcome solubility issues, some formulations use solvents with amounts of VOCs that are not safe for the environment. For example, isopropyl alcohol and methyl alcohol offer severe disadvantages such as flammability and toxicity, which lead to restrictions in manufacturing, packaging, labeling, transportation, and warehousing of such solutions. Tetrahydrofurfuryl alcohol ("THFA") is considered corrosive to the eye and skin.

Moreover, the low solubility of $GA_3$, $GA_4$, and $GA_{4/7}$ in some solvents, such as propylene glycol, does not permit preparation of high potency solution formulations. These low strength solution formulations require larger packaging, more storage space, and higher associated transportation, warehousing, and container disposal costs. Due to very low solubility and undesirable hydrolysis, it has been especially difficult to formulate $GA_3$ in aqueous systems.

One way to overcome the solubility issues with $GA_3$, $GA_4$, and $GA_{4/7}$ is to prepare soluble powder formulations. These powder formulations dissolve readily when mixed with water and form true solutions. Once the solution is formed, no further mixing or agitation of the tank-mix is required.

Another way to overcome the solubility issues is to create a wettable powder. A wettable powder formulation is a dry, finely ground formulation. In this type of formulation, the active ingredient is combined with a finely ground dry carrier, usually a mineral clay, along with other ingredients that enhance the ability of the powder to be suspended in water. Upon mixing the wettable powder with water, a suspension is formed, which is then applied by a spray technique. Often the spray liquid must be continuously mixed to prevent settling of insoluble compositions.

However, wettable powders and soluble powder formulations tend to produce dust upon handling, such as when pouring, transferring or measuring them. This dust may pose health hazards. Further, powder formulations tend to wet poorly and also solubilize slowly upon addition to water. Powder formulations thus take longer times to wet, disperse and solubilize in the tank-mix. Formation of lumps or partially solubilized spray solutions will lead to uneven distribution of the plant growth regulator in the tank-mix with potential for reduced field performance. Sometimes, foam in the spray tank caused by spray tank adjuvants can also affect wetting and solubility of wettable and soluble powders. Wettable powder formulations will also leave undesirable insoluble residues both in the tank and on the sprayed foliage and fruit.

Another type of agricultural formulation is a tablet. Tablet formulations are pre-measured dosage delivery systems. They are useful in small areas, or for ornamental purposes. Tablet formulations may be effervescent, which dissolve in water over a period of two to ten minutes depending upon the type and size of the tablet. However, tablets generally deliver only between 0.1 to 1 gram of active ingredient per tablet. They are not ideal for large-scale field operations. Moreover, effervescent tablets are highly susceptible to humidity and may be slow to dissolve and are expensive.

Yet another type of agricultural formulation is a water-dispersible granule. Water-dispersible granules are also known as wettable granules or dry flowables. This type of formulation is similar to a wettable powder, except that the active ingredient is formulated as a dispersible granule. To prepare the water-dispersible granules for spray application, they are dispersed in water and form a suspension upon agitation. Many different water-dispersible granular formulations are known for agricultural chemicals. For example, EP 0 252 897 and U.S. Pat. No. 4,936,901 disclose encapsulated plant growth regulators in water dispersible granular formulations; and U.S. Pat. No. 5,622,658 discloses an extrudable composition for preparing water-dispersible granules.

Water-dispersible granules usually have no greater than eight percent moisture content, and form suspensions when added to aqueous solutions. The resulting suspension must be agitated for a period of time in order to fully disperse it. Agitation or by-pass recirculation of the tank-mix must also be maintained during application. The quality of water-dispersible granules is highly process- and active-ingredient-dependent; and can result in low yield recoveries, poor attrition resistance leading to dust potential, high manufacturing cost and poor dispersion. Generally, sprays of dissolved water-dispersible granular formulations leave undesirable insoluble residues on the treated foliage and fruit.

For $GA_3$, $GA_4$, and $GA_{4/7}$ formulations to be efficacious, the active ingredient must solubilize in tank-mixes prior to application. Otherwise, product efficacy will be severely affected. When water-dispersible granules are used, the grower often may not know when he has achieved the total solubility of the active ingredient in the spray solutions. In addition, water-dispersible granules can harden over time and thus result in poor dispersibility and solubility of the active ingredient. In addition, dust and caking may be problems with certain water-dispersible granules and powder formulations.

Currently, there is a strong market demand for high quality table grapes. One way to obtain grape berries of sufficient size is to thin the vines. There is a need for a consistent chemical thinning material that will improve berry cluster quality in order to save the costs of manually thinning each grape berry cluster. U.S. Pat. No. 6,984,609 discloses a concentrated, water-soluble, granular plant growth regulator formulation that is commercially available as ProGibb® 40% (available from Valent BioSciences Corp., ProGibb is a registered trademark of Valent BioSciences Corp.). The disclosed granules swiftly dissolve in water and provide a true solution without any insoluble particulates in the spray mixture. ProGibb® 40% is a reliable chemical thinner for grape vines. However, some orchard growers would prefer solution formulations that are easier to apply.

Therefore, there is a need for environmentally safe, non-phytotoxic, efficacious, high strength gibberellin solution formulations. The improved formulations should overcome the toxicity, handling, storage, transportation, human exposure, and solubility issues encountered by prior art formulations. The formulations should also include low amounts of VOCs in order to be environmentally safe and be safer for growers to tank mix prior to application. In addition, the formulations should provide consistent thinning on grape vines when applied at effective amounts.

SUMMARY OF THE INVENTION

The present invention is directed toward $GA_3$, $GA_4$ and $GA_{4/7}$ solution formulations that have low VOC levels.

In one aspect, the invention is directed to liquid agricultural formulations comprising from about 1 to about 10% of at least one gibberellin selected from the group consisting of $GA_3$, $GA_4$, and $GA_{4/7}$, from about 85 to about 99% polyethylene glycol with a molecular weight from about 190 to about 420, and from about 0.1 to about 5% of a non-ionic or anionic surfactant, wherein the formulation does not include isopropyl alcohol, and wherein the percentages are percent by weight of the formulation.

In another aspect, the invention is directed to methods for regulating plant growth comprising the step of treating a seed, soil or a plant with an effective amount of the formulations of the present invention.

DETAILED DESCRIPTION OF THE INVENTION

Applicants have discovered that a formulation comprising from about 1 to about 10% of at least one gibberellin selected from the group consisting of $GA_3$, $GA_4$, and $GA_{4/7}$, from about 85 to about 99% polyethylene glycol with a molecular weight from about 190 to about 420, and from about 0.1 to about 5% of a non-ionic or anionic surfactant provides an effective agricultural formulation which has low levels of VOCs and, accordingly, is environmentally safe. Applicants' formulations are also storage stable and non-phytotoxic while being efficacious.

In one embodiment, the present invention is directed to liquid agricultural formulations comprising from about 1 to about 10% of at least one gibberellin selected from the group consisting of $GA_3$, $GA_4$, and $GA_{4/7}$, from about 85 to about 99% polyethylene glycol with a molecular weight from about 190 to about 420, and from about 0.1 to about 5% of a non-ionic or anionic surfactant, wherein the formulation does not include isopropyl alcohol, and wherein the percentages are percent by weight of the formulation.

In a preferred embodiment, the invention is directed to liquid agricultural formulations comprising from about 1 to about 10% $GA_3$, from about 85 to about 99% polyethylene glycol with a molecular weight from about 190 to about 420, and from about 0.1 to about 5% of a non-ionic or anionic surfactant, wherein the formulation does not include isopropyl alcohol, and wherein the percentages are percent by weight of the formulation.

In another preferred embodiment, the invention is directed to liquid agricultural formulations comprising from about 1 to about 10% $GA_3$, from about 85 to about 99% polyethylene glycol with a molecular weight from about 190 to about 210, and from about 0.1 to about 5% of a non-ionic or anionic surfactant, wherein the formulation does not include isopropyl alcohol, and wherein the percentages are percent by weight of the formulation.

In yet another embodiment, the invention is directed to liquid agricultural formulations comprising from about 1 to about 10% $GA_4$, from about 85 to about 99% polyethylene glycol with a molecular weight from about 190 to about 210, and from about 0.1 to about 5% of a non-ionic or anionic surfactant, wherein the formulation does not include isopropyl alcohol, and wherein the percentages are percent by weight of the formulation.

In yet another embodiment, the invention is directed to liquid agricultural formulations comprising from about 1 to about 10% $GA_{4/7}$, from about 85 to about 99% polyethylene glycol with a molecular weight from about 190 to about 210, and from about 0.1 to about 5% of a non-ionic or anionic surfactant, wherein the formulation does not include isopropyl alcohol, and wherein the percentages are percent by weight of the formulation.

In an embodiment, the non-ionic or anionic surfactant of the present invention is a polysorbate surfactant. In a preferred embodiment, the polysorbate surfactant is a polysorbate surfactant with 20 moles of ethylene oxide per mole of sorbitol.

In another embodiment, the invention is directed to liquid agricultural formulations comprising from about 2 to about 9% $GA_3$, from about 88 to about 98% polyethylene glycol with a molecular weight from about 190 to about 210, from about 285 to about 315, or from about 380 to about 420, or a combination thereof, and from about 0.1 to about 2% of the non-ionic or anionic surfactant, wherein the formulation does not include isopropyl alcohol, and wherein the percentages are percent by weight of the formulation.

In an embodiment, the invention is directed to liquid agricultural formulations comprising from about 4.2 to about 7% $GA_3$, from about 89 to about 97% polyethylene glycol with a molecular weight from about 190 to about 210, from about 285 to about 315, or from about 380 to about 420, or a combination thereof, and from about 0.3 to about 0.5% of the non-ionic or anionic surfactant, wherein the formulation does not include isopropyl alcohol, and wherein the percentages are percent by weight of the formulation.

In another embodiment, the invention is directed to liquid agricultural formulations comprising from about 5.4 to about 6% $GA_3$, from about 90.5 to about 96% polyethylene glycol with a molecular weight from about 190 to about 210, from about 285 to about 315, or from about 380 to about 420, or a combination thereof, and from about 0.3 to about 0.5% of the non-ionic or anionic surfactant, wherein the formulation does not include isopropyl alcohol, and wherein the percentages are percent by weight of the formulation.

In yet another embodiment, the invention is directed to liquid agricultural formulations comprising about 5.9% $GA_3$, about 93% polyethylene glycol with a molecular weight from about 190 to about 210, from about 285 to about 315, or from about 380 to about 420, or a combination thereof, and about 0.4% of the non-ionic or anionic surfactant, wherein the formulation does not include isopropyl alcohol, and wherein the percentages are percent by weight of the formulation.

In one embodiment, the present invention is directed to liquid agricultural formulations consisting of from about 1 to about 10% of at least one gibberellin selected from the group consisting of $GA_3$, $GA_4$, and $GA_{4/7}$, from about 85 to about 99% polyethylene glycol with a molecular weight from about 190 to about 420, and from about 0.1 to about 5% of a non-ionic or anionic surfactant, wherein the percentages are percent by weight of the formulation.

In an embodiment, the present invention is directed to liquid agricultural formulations consisting of from about 4.2 to about 7% of at least one gibberellin selected from the group consisting of $GA_3$, $GA_4$, and $GA_{4/7}$, from about 89 to about 97% polyethylene glycol with a molecular weight from about 190 to about 210, from about 285 to about 315, or from about 380 to about 420, and from about 0.3 to about 0.5% of the non-ionic or anionic surfactant.

In yet another embodiment, the present invention is directed to liquid agricultural formulations consisting of from about 5.4 to about 6% of at least one gibberellin selected from the group consisting of $GA_3$, $GA_4$, and $GA_{4/7}$, from about 90.5 to about 96% polyethylene glycol with a molecular weight from about 190 to about 210, from about 285 to about 315, or from about 380 to about 420, and from about 0.3 to about 0.5% of the non-ionic or anionic surfactant.

In another embodiment, the present invention is directed to liquid agricultural formulations consisting of from about 5.7% of at least one gibberellin selected from the group consisting of $GA_3$, $GA_4$, and $GA_{4/7}$, about 93.3% polyethylene glycol with a molecular weight from about 190 to about 210, from about 285 to about 315, or from about 380 to about 420, and about 0.4% of the non-ionic or anionic surfactant.

In an embodiment, the present invention is directed to liquid agricultural formulations consisting of from about 1 to about 10% $GA_3$, from about 85 to about 99% polyethylene glycol with a molecular weight from about 190 to about 420, and from about 0.1 to about 5% of a non-ionic or anionic surfactant, wherein the percentages are percent by weight of the formulation.

In another embodiment, the present invention is directed to liquid agricultural formulations consisting of from about 1 to about 10% $GA_4$, from about 85 to about 99% polyethylene glycol with a molecular weight from about 190 to about 210, and from about 0.1 to about 5% of a non-ionic or anionic surfactant, wherein the percentages are percent by weight of the formulation.

In an embodiment, the present invention is directed to liquid agricultural formulations consisting of from about 1 to about 10% $GA_{4/7}$, from about 85 to about 99% polyethylene glycol with a molecular weight from about 190 to about 210, and from about 0.1 to about 5% of a non-ionic or anionic surfactant, wherein the percentages are percent by weight of the formulation.

In one embodiment, the present invention is directed to liquid agricultural formulations consisting of from about 1 to about 10% of at least one gibberellin selected from the group consisting of $GA_3$, $GA_4$, and $GA_{4/7}$, from about 85 to about 99% polyethylene glycol with a molecular weight from about 190 to about 210, and from about 0.1 to about 5% of a non-ionic or anionic surfactant, wherein the percentages are percent by weight of the formulation.

In a final embodiment, the invention is directed to methods of regulating plant growth comprising the step of treating a seed, soil or a plant with an effective amount of the formulations of the present invention.

Polyethylene glycol ("PEG") is a is a polyether compound with the structure: H—(O—$CH_2$—$CH_2$)$_n$—OH. PEGs are prepared by polymerization of ethylene oxide and are commercially available over a wide range of molecular weights up to 10,000,000 g/mol. The number following "polyethylene glycol", or "PEG", refers to the molecular weight. For example, PEG 200 has a range of molecular weights from 190 to 210, PEG 300 from 285 to 315, and PEG 400 from 380 to 420 g/mol. Preferably, the PEG is from about 85 to 99% by weight of the formulation. In a more preferred embodiment, the PEG is from about 88 to 98%, 89 to 97%, or 90.5 to 96% by weight of the formulation. In a most preferred embodiment, the PEG is about 93% by weight of the formulation.

Polyethylene glycol 200 is used in the formulations of the present invention as a diluent/solvent. For example, Pluriol® E 200 (Pluriol is a registered trademark of BASF) can be used to form the stable, environmentally safe formulations of the present invention. Pluriol® E 200 is available from BASF Corporation. Polyethylene glycol is also available under various brand names for example: Carbowax 200 from Dow Chemical; Macrogol 200 from NOF North America Corporation; and Ultrapeg 200 from OxiTeno. PEG 200 is an ideal solvent of choice due to many of its desirable properties such as high flash point (>171° C.), low vapor pressure (<0.01 mmHg @20° C.), non-volatile properties at room temperature, low viscosity (4.0-4.3 cSt @99° C.), excellent water solubility in any ratio, solvency power, outstanding toxicological and environmental safety. PEG 200 has many food, cosmetic, and pharmaceutical uses. PEG 200 may also be combined with other suitable low VOC solvents such as PEG 300 and PEG 400.

Polyethylene glycol 300 is also used in the formulations of the present invention as a diluent/solvent. Pluriol® E 300 (Pluriol is a registered trademark of BASF) can be used to form the stable, environmentally safe formulations of the present invention. Pluriol® E 300 is available from BASF Corporation.

Polyethylene glycol 400 is also used in the formulations of the present invention as a diluent/solvent. Pluriol® E 400 (Pluriol is a registered trademark of BASF) can be used to form the stable, environmentally safe formulations of the present invention. Pluriol® E 400 is available from BASF Corporation.

Non-ionic or anionic surfactants can be used in formulations of the present invention. Surfactants that could be used include, but are not limited to, sorbitan derivatives such as Tween® 80, Tween® 85 (Tween® is a registered trademark of Croda Americas, Inc., Tween® 80 and 85 are available from Croda, Inc.), ethoxylated alcohols such as Brij® 98 (Brij® is a registered trademark of Uniqema Americas LLC, Brij® 98 is available from Croda Inc.), ethoxylated alkylphenols such as Igepol CA-630, Igepol, and Igepol CO-630 from Rhodia Inc., ethoxylated fatty acids such as Myrj® 52 (Myrj® is a registered trademark of Atlas Powder Company, Myrj® 52 is available from Croda Inc.), silicone based surfactants such as Silwet L-77® (Silwet and Silwet L-77 are registered trademarks of Momentive Performance Chemicals, Silwet L-77® is available from Momentive Performance Chemicals), and block polymeric surfactants such as Pluronic® P85 and Pluronic® P104 (Pluronic is a registered trademark of BASF Corporation, Pluronic® P85 and P104 are available from BASF Corporation). The percent surfactant in the formulation may range from 0.1 to 5% by weight depending upon the desired formulation characteristics and end use. Preferably, the surfactant is from about 0.1 to about 4, from about 0.1 to about 3, from about 0.1 to about 2, from about 0.1 to about 1, or from about 0.3 to about 0.5% by weight of the formulation. In a most preferred embodiment, the surfactant is about 0.4% by weight of the formulation.

Preferably, polysorbate surfactants are used in the formulations of the present invention. Polysorbate surfactants are produced by reacting the polyol sorbitol with ethylene dioxide. The number that follows "polysorbate" refers to the number of moles of ethylene dioxide that has been reacted per mole of sorbitol. The polyoxyethylenated sorbitan is then reacted with fatty acids obtained from vegetable fats and oils such as lauric acid, palmitic acid, stearic acid, and oleic acid. Examples of polysorbate surfactants include polysorbate 20, polysorbate 40, polysorbate 60, and polysorbate 80. One preferred polysorbate surfactant is polysorbate 20.

Polysorbate 20 is a nonionic surfactant that is used in the formulations of the present invention as a surfactant. For example, Tween® 20 can be used to form the stable, environmentally safe formulations of the present invention. Tween® 20 is available from Croda, Inc.

The formulations of the present invention do not contain isopropyl alcohol. Isopropyl alcohol is considered a VOC by the US Environmental Protection Agency ("EPA") and by the European Union (with a boiling point of 82.6° C.). As explained above, limitations of isopropyl alcohol formulations include flammability and toxicity, which lead to restrictions in manufacturing, packaging, labeling, transportation, and warehousing of such formulations. Isopropyl alcohol is explicitly excluded from the formulations of the present invention in order to avoid these formulation limitations. Isopropyl alcohol is also excluded from the present formulations because the present formulations are low VOC and safer for the environment than prior art formulations.

Applicants found that the formulations of the present invention were very effective on grapes. Formulations of the present invention may be used on any plant in need of gibberellin treatment, for example, on: artichokes to accelerate maturity and increase yield; blueberries to improve fruit set and fruit size; bananas to stimulate plant growth and reduce effects of stress, or post-harvest for maintaining fruit quality; carrots to maintain foliage growth during periods of stress; celery to increase plant height and yield; cherries to increase fruit size, firmness and quality or to delay maturity for a more orderly harvest; citrus to increase fruit set and yield, to delay rind aging, reduce physiological disorders, or delay maturity for a more orderly harvest; collard greens to facilitate harvest, increase yield, and improve quality; cotton to promote early season growth and increase seedling vigor; and cucumbers to stimulate fruit set during periods of cool weather; pasture land used for animal grazing; and corn. The formulations can be used post harvest on bananas and citrus, etc. Formulations of the present invention could also be used on grapes, melons, pecans, peppers, pineapples, rice, rhubarb, spinach, stone fruits, strawberries, watercress and other plants in need of treatment.

Formulations of the present invention can also be used as a seed treatment.

Applicants also found that the formulations of the present invention have excellent storage stability characteristics when subjected to accelerated stability testing.

The disclosed embodiments are simply exemplary embodiments of the inventive concepts disclosed herein and should not be considered as limiting, unless the claims expressly state otherwise.

The present invention is also directed to methods of regulating plant growth comprising the step of treating soil, a seed or a plant with an effective amount of the formulations described above. The formulation may be diluted with water and spray-applied. For example, when the plant is a fruit-producing plant, such as a grape plant, a grape-producing plant so treated produces larger grapes and/or grapes having higher percentage of soluble solids.

In a preferred embodiment, the formulation of the present invention is applied to grape vines to reduce the number of grape berries per cluster that reach maturity. In a more preferred embodiment, the formulation of the present invention is applied to the grapes vines when the grape berries are less than 13 mm in diameter.

The term "effective amount" means the amount of the formulation that will provide the desired effect on the plant that is being treated. The "effective amount" will vary depending on the formulation concentration, the type of plants(s) being treated, and the result desired, among other factors. Thus, it is not always possible to specify an exact "effective amount." However, an appropriate "effective amount" in any individual case may be determined by one of ordinary skill in the art. For example, effective amounts of formulations of the present invention may be from about 1 to about 10% of gibberellin, and more preferably from about 2.9% to about 4% gibberellin or from about 5.7% to about 7.1% gibberellin.

Other plant growth regulators may be used in similar formulations to achieve stable and environmentally safe formulations. The phrase "plant growth regulator" as used herein connotes a product which serves to modify the growth and the development of a treated plant to agricultural maturity without killing the plant. Such modification may result from the effect of the material on the physiological processes of the plant, or from the effect of said material on the morphology of the plant. These modifications may also result from any combination or sequence of physiological or morphological factors.

Although gibberellin formulations are exemplified herein, the plant growth regulator may be used such as, a cytokinin such as TDZ, Kinetin, or 6-benzyladenine, an auxin, an organic acid, an ethylene biosynthesis inhibitor, or a combination thereof.

As mentioned above, formulations of the present invention have low levels of VOCs. Other diluents and surfactants may be in formulations of the present invention as long as the diluents and surfactants are "environmentally safe," meaning that they are exempt from VOC regulation by the Environmental Protection Agency. The agricultural formulations of the present invention explicitly exclude organic solvents which are considered to have unsatisfactory VOC levels as defined by California Environmental Protection Agency. The agricultural formulations of the present invention explicitly exclude isopropyl alcohol. Further, the agricultural formulations of the present invention explicitly exclude ingredients which are considered by the state of California to cause cancer or reproductive toxicity under The Safe Drinking Water and Toxic Enforcement Act of 1986 (see Health and Safety Code Section 25249.8(b)).

Other components of the formulation may be included in nominal amounts that do not affect the storage stability or low VOC characteristics of the present formulations. Additional components include surface active agents, crystal growth inhibitors, stickers, spreaders, leaf penetrants, dispersants, systemic acquired resistance inducers, systemic acquired resistance inhibiters, anti-foaming agents, preservatives, pH regulators, cosolvents, humectants, dyes, UV protectants, vehicles, sequestrants or other components which facilitate production, storage stability, product handling and application.

It is also contemplated that the ready-to-mix composition materials of this invention may be used in combination with other active ingredients, such as herbicides, fungicides, insecticides, bactericides, nematicides, biochemical pesticides, plant produced pesticides (botanicals), safeners or plant nutrients.

As used herein, the term "herbicide" broadly refers to compounds or compositions that are used as herbicides, as well as herbicide safeners and algicides. Herbicides may include, but are not limited to, 1,2,4-triazinones, 1,3,5-triazines, alkanamides (acetamides), anilides, aryloxyalkanoic acids, aryloxyphenoxypropionates, benzamides, benzamides (L), benzenedicarboxylic acids, benzofurans, benzoic acids (auxins), benzonitriles, benzothiadiazinones, benzothiazolones, carbamates (DHP), carbamates, chloroacetamides, cyclohexanedione oximes, dinitroanilines, dinitrophenols, diphenyl ethers, diphenyl ethers (cbi), glycine derivatives, halogenated alkanoic acids, hydroxybenzonitriles, imidazolinones, isoxazoles, isoxazolidinones, N-phenylphthalimides, organoarsenics, oxadiazoles, oxazolidinediones, oxyacetamides, phenoxycarboxylic acids, phenyl carbamate herbicides, phenylpyrazole herbicides, phenylpyridazines, phosphinic acids, phos-phorodithioates, phthalamates, pyrazole herbicides, pyridazines, pyridazinones (PDS), pyridazinones (PSII), pyridines, pyridinecarboxamides, pyridinecarboxylic acids, pyrimidindiones, pyrimidines, pyrimidinyl-oxybenzoics, pyrimidinyloxybenzoic analogs, quinolinecarboxylic acids, BI class IV: thiocarbamate, semi-carbazones, sulfonylaminocarbonyl-triazolinones, sulfonylureas, tetrazolinones, thiadiazoles, thiocarbamates, triazoles, triazolinones, triazolopyrimidines, triketones, uracils, and ureas. Suitable herbicides include 2,3,6-TBA, 2,4,5-T, 2,4-D, 2,4-D-2-ethylhexyl, 2,4-DB, 2,4-D-dimethylammonium, 2,4-D-isopropyl, 2,4-D-isopropyl, 2,4-D-trolamine (2,4-D-triethanolamine), ACD 10614; ACD 10435, acetochlor, acifluorfen, acifluorfen-sodium, aclonifen, acrolein, AD 67, alachlor, alloxydim-sodium, ametryn, amicarbazone, amidosulfuron, amitrole, ammonium sulfamate, anilofos, asulam, atraton, atrazine, azafenidin, azimsulfuron, aziprotryne, barban, beflubutamid, benazolin, benazolin-ethyl, benfluralin, benfuresate, benoxacor, bensulfuron-methyl, bensulide, bentazone, benzobicyclon, benzofenap, benzoylprop, enzoylprop-ethyl, bifenox, bilanafos-sodium, bispyribac-sodium, borax, bromacil, bromobutide, bromofenoxim, bromoxynil, bromoxynil octanoate, bromoxynil-potassium, brompyrazon, butachlor, butafenacil, butenachlor, buthidazole, butralin, butroxydim, buturon, cafenstrole, calcium cyan-amide, carbetamide, carfentrazone-ethyl, chlomethoxyfen, chloramben, chlorbromuron, chlorbufam, chlorfenac, chlorfenac-sodium, chlorfenprop, chlorfenprop-methyl, chlorfenprop, chlorfenprop-ethyl, chlorflurenol-methyl, chloridazon, chlorimuron-ethyl, chlornitrofen, chloroacetic acid, chloro-toluron, chloroxuron, chlorpropham, chlorsulfuron, chlorthal-dimethyl, chlorthiamid, cinidon-ethyl, cinosulfuron, clodinafop-propargyl, clofop, clofop-isobutyl, clomazone, clomeprop, clopyralid, cloquintocet-mexyl, cloransulam-methyl, credazine, cumyluron, cyanamide, cyanazine, cyclosulfamuron, cycloxydim, cycluron, cyhalofop-butyl, cyometrinil, daimuron, dazomet, desmedipham, desmetryn, di-allate, dicamba, dichlobenil, dichlormid, dichlorprop, dichlorprop-isoctyl, dichlorprop-P, diclofop, diclofop-methyl, diclosulam, diethatyl-ethyl; diethatyl, difenoxuron, difenzoquat metilsulfate, diflufenican, diflufenzopyr, dikegulac, dikegulac-sodium, dimefuron, dimepiperate, dimethachlor, dimethametryn, dimethipin, dimethylarsinic acid, dinitramine dinoseb, dinoseb acetate, dinoterb, diphenamid, dipropetryn, disul, disul-sodium, dithiopyr, diuron, DNOC, DSMA, eglinazine-ethyl, eglinazine, EL 177, endothal, ethalfluralin, ethametsulfuron-methyl, ethidimuron, ethofumesate, ethoxysulfuron, etobenzanid, fenchlorazole-ethyl, fenclorim, fenoprop, fenoprop-butotyl, fenoxaprop-ethyl, fenoxaprop, fenoxaprop-P, fenoxaprop-P-ethyl, fenthiaprop; fenthiaprop-ethyl, fentrazamide, fenuron, flamprop-methyl, flamprop-isopropyl, flamprop, flamprop-M-isopropyl, flamprop-M-methyl, flazasulfuron, florasulam, fluazifop-butyl, fluazifop-P, fluazifop-P-butyl, fluazolate, flucarbazone-sodium, fluchloralin, flufenacet, flumetsulam, flumiclorac-pentyl, flumioxazin, flumipropyn, fluometuron, fluorodifen, fluoroglycofen-ethyl, fluothiuron, flupoxam, flupropanate-sodium, flupyr-sulfuron-methyl-sodium, flurazole, flurenol-butyl, fluridone, flurochloridone, fluroxypyr, fluroxypyr-meptyl, flurtamone, fluthiacet-methyl, fomesafen, foramsulfuron, fosamine-ammonium, furilazole, glufosinate-ammonium, glyphosate, glyphosate-ammonium, glyphosate-isopropylammonium, glyphosate-sodium, glyphosate-trimesium, halosulfuron-methyl, haloxyfop, haloxyfop-etotyl, haloxyfop-P, hexaflurate, hexazinone, imazamethabenz-methyl, imazamox, imazapic, imazapyr, imazapyr-isopropylammonium, imazaquin, imazethapyr, imazosulfuron, indanofan, iodosulfuron-methyl-sodium, ioxynil, ioxynil octanoate, ioxynil-sodium, isocarbamid, isocil, isomethiozin, isonoruron, isoproturon, isouron, isoxaben, isoxaflutole, isoxapyrifop, karbutilate, lactofen, lenacil, linuron, LS830556, maleic hydrazide, MCPA, MCPA-thioethyl, MCPB, MCPB-ethyl, mecoprop, mecoprop-P, medinoterb acetate, medinoterb, mefenacet, mefenpyr-diethyl, mefluidide, mesosulfuron-methyl, mesotrione, metamifop, metamitron, metazachlor, methabenzthiazuron, methazole, methiuron, methoprotryne, methoxyphenone, methyl isothiocyanate, methylarsonic acid, methyldymron, metobenzuron, metobromuron, metolachlor, metosulam, metoxuron, metribuzin, metsulfuron-, ethyl, MK-616, monalide, monolinuron, monuron, monuron-TCA, MSMA, naphthalic anhydride, naproanilide, napropamide, naptalam, NC-330, neburon, nicosulfuron, nitralin, nitrofen, nonanoic acid, norflurazon, oleic acid (fatty acids), orbencarb, oryzalin, oxabetrinil, oxadiargyl, oxadiazon, oxasulfuron, oxaziclomefone, oxyfluorfen, pendimethalin, penoxsulam, pentachloro-phenol, pentanochlor, pentoxazone, perfluidone, pethoxamid, phen-isopham, phenmedipham, phenylmercury acetate, picolinafen, primisulfuron-methyl, prodiamine, profluralin, proglinazine-ethyl, proglinazine, prometon, prometryn, propachlor, propanil, propaquizafop, propazine, propham, propisochlor, propoxycarbazone-sodium, propyzamide, prosulfuron, pyraflufen-ethyl, pyrazolynate, pyrazosulfuron-ethyl, pyrazoxyfen, pyribenzoxim, pyributicarb, pyridate, pyriftalid, pyriminobac-methyl, pyrithiobac-sodium, quinclorac, quinmerac, quinoclamine, quizalofop-ethyl, quizalofop-P-ethyl, quizalofop-P-tefuryl, rimsulfuron, sebuthylazine, secbumeton, siduron, simazine, simetryn, S-metolachlor, SMY 1500, sodium chlorate, sulcotrione, sulfentrazone, sulfometuron-methyl, sulfosulfuron, tebuthiuron, tepraloxydim, terbacil, terbumeton, terbuthylazine, terbutryn, thenylchlor, thiazafluron, thiazopyr, thidiazimin, thifensulfuron-methyl, thiobencarb, 1-dichloroacetylazepane, tralkoxydim, tri-allat, triasulfuron, tribenuronmethyl, trichloroacetic acid, triclopyr, tridiphane, trietazine, trifloxysulfuron-sodium, trifluralin, and triflusulfuron-methyl.

Fungicides may include, but are not limited to, amino acid amide carbamates, anilinopyrimidines, antibiotics, aromatic hydrocarbons, heteroaromatics, chloro/nitrophenyls, benzamides (F), benzenesulfonamides, benzimidazoles, benzimidazole precursors, benzotriazines, carboxamides, cinnamic acids, cyanoacetamide oximes, dicarboximides, dithiolanes, DMI: imidazoles, DMI: piperazines, DMI: pyrimidines, DMI: triazoles, enopyranuronic acid antibiotics, heteroaromatic hydroxyanilides, MBI: dehydratases, MBI: reductases, morpholine: morpholines, morpholine: spiroketalamines, multi-site: chloronitriles, multi-site: dimethyldithiocarbamates, multi-site: guanidines, multi-site: inorganics, multi-site: phthalimides, multi-site: quinones, multi-site: sulfamides, N-phenyl carbamate fungicides, organotin fungicides, phenylamide: acylalanines, phenylamide: butyrolactones, phenylamide: oxazolidinones, phenylpyrroles, phenylurea fungicides, phosphonates, phosphorothiolates, pyridazinone fungicides, pyrimidinamines, pyrimidinols, QiI, quinolines, SBI class IV: thiocarbamates, strobilurin analog: dihydrodioxazines, strobilurin type: imidazolinones, strobilurin type: methoxyacrylates, strobilurin type: ethoxycarbamates, strobilurin type: oxazolidinediones, strobilurin type: oximinoacetamides, strobilurin type: oximinoacetates, thiazolecarboxamides, thiocarbamate fungicides, and thiophenecarboxamides. Suitable fungicides include 1,2-dichloro-propane, 2-methoxyethylmercury chloride, 2-phenylphenol, 8-hydroxy-quinoline sulfate, ampropylfos, anilazine, azaconazole, azoxystrobin, benalaxyl, benodanil, benomyl, benquinox, benthiavalicarb-isopropyl, binapacryl, biphenyl, bis(tributyltin) oxide, bitertanol, blasticidin-S, borax, boscalid, bromuconazole, bupirimate, buthiobate, captafol, captan, carbendazim, carboxin, carpropamid, CGA 80 000, chinomethionat, chlobenthiazone, chloraniformethan, chloroneb, chlorothalonil, chlozolinate, climbazole, copper oxychloride, copper sulfate, copper sulfate (tribasic), cuprous oxide, cyazofamid, cyflufenamid, cymoxanil, cyproconazole, cyprodinil, cyprofuram, dazomet, dichlofluanid, dichlone, dichlorophen, diclobutrazol, diclocymet, diclomezine, dicloran, diethofencarb, difenoconazole, difenzoquat metilsulfate, diflumetorim, dimethirimol, dimethomorph, dimoxystrobin, diniconazole, dinobuton, dinocap, diphenylamine, ditalimfos, dithianon, dodemorph, dodemorph acetate, dodine, drazoxolon, edifenphos, epoxiconazole, etaconazole, etem, ethaboxam, ethirimol, etridiazole, famoxadone, fenamidone, fenarimol, fenbuconazole, fenfuram, fenhexamid, fenitropan, fenoxanil, fenpiclonil, fenpropimorph, fentin acetate, fentin hydroxide, ferimzone, fluazinam, fludioxonil, flumorph, fluoroimide, fluotrimazole, fluoxastrobin, fluquinconazole, flusilazole, flusulfamide, flutolanil, flutriafol, folpet, fosetyl-aluminum, fuberidazole, furalaxyl, furametpyr, furconazole-cis, furmecyclox, glyodin, griseofulvin, halacrinate, hexachlorobenzene, hexaconazole, hymexazol, imazalil, imibenconazole, iminoctadine triacetate, iminoctadine tris(albesilate), ipconazole, iprodione, iprovalicarb, isoprothiolane, kasugamycin hydrochloride hydrate, kresoxim-methyl, mebenil, mepanipyrim, mepronil, mercuric chloride, metalaxyl, metalaxyl-M, metconazole, methasulfocarb, methfuroxam, methyl iodide, methyl isothiocyanate, metominostrobin, metsulfovax, mildiomycin, myclobutanil, myclozolin, natamycin, nitrothal-isopropyl, nuarimol, ofurace, oleic acid, fatty acids), oxabetrinil, oxadixyl, oxpoconazole fumarate, oxycarboxin, penconazole, pencycuron, pentachlorophenol, phenylmercury acetate, phenylmercury dimethyldithiocarbamate, phenylmercury nitrate, phosphonic acid, phthalide, picoxystrobin, polyoxin B, polyoxorim, potassium bicarbonate, potassium hydroxyquinoline sulfate, prochloraz, procymidone, propamocarb hydrochloride, propiconazole, proquinazid, prothiocarb; prothiocarb hydrochloride, prothioconazole, pyracarbolid, pyraclostrobin, pyrazophos, pyributicarb, pyrimethanil, pyroquilon, quinoclamine, quinoxyfen, quintozene, silthiofam, simeconazole, sodium bicarbonate, spiroxamine, SSF-109, sulfur, tebuconazole, tecnazene, tetraconazole, thiabendazole, thicyofen, thifluzamide, thiophanate, thiophanate-methyl, thiram, tiadinil, tolclofos-methyl, tolylfluanid, triadimefon, triadimenol, triamiphos, triazoxide, trichlamide, tricyclazole, trifloxystrobin, triflumizole, triforine, triticonazole, urbacid, validamycin, vinclozolin, zarilamid, ziram, and zoxamide.

Bactericides may include, but are not limited to, bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulfate and other copperpreparations.

Insecticides, acaricides and nematicides may include, but are not limited to, abamectin, ABG-9008, acephate, acequinocyl, acetamiprid, acetoprole, acrinathrin, AKD-1022, AKD-3059, AKD-3088, alanycarb, aldicarb, aldoxycarb, allethrin, alpha-cypermethrin (alphamethrin), amidoflumet, aminocarb, amitraz, avermectin, AZ-60541, azadirachtin, azamethiphos, azinphos-methyl, azinphos-ethyl, azocyclotin, *Bacillus firmus*, *Bacillus popilliae*, *Bacillus sphaericus*, *Bacillus subtilis*, *Bacillus thuringiensis*, *Bacillus thuringiensis* strain EG-2348, *Bacillus thuringiensis* strain GC-91, *Bacillus thuringiensis* strain NCTC-11821, *Bacillus thuringiensis israelensis*, baculoviruses, *Beauveria bassiana*, *Beauveria tenella*, benclothiaz, bendiocarb, benfuracarb, bensultap, benzoximate, beta-cyfluthrin, beta-cypermethrin, bifenazate, bifenthrin, binapacryl, bioallethrin, bioallethrin-S-cyclopentyl isomer, bioethanomethrin, biopermethrin, bioresmethrin, bistrifluoron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, chinomethionat, chlorantraniliprole, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cisresmethrin, cis-permethrin, clocythrin, cloethocarb, clofentezine, clothianidin, clothiazoben, codlemone, coumaphos, cyanofenphos, cyanophos, cyantraniliprole, cycloprene, cycloprothrin, cyfluthrin, cyflumetofen, cyhalothrin, cyhexatin, cypermethrin, cyphenothrin (1R-trans-isomer), cyromazine, DDT, deltamethrin, demeton-S-methyl, demeton-S-methylsulfone, diafenthiuron, dialifos, diazinon, dichlofenthion, dichlorvos, dicofol, dicrotophos, dicyclanil, diflubenzuron, dimefluthrin, dimethoate, dimethylvinphos, dinobuton, dinocap, dinotefuran, diofenolan, disulfoton, docusat-sodium, dofenapyn, DOWCO-439, eflusilanate, emamectin, emamectin-benzoate, empenthrin (1R-isomer), endosulfan, Entomopthora spp., EPN, esfenvalerate, ethiofencarb, ethion, ethiprole, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubendiamide, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-cyhalothrin, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methacrifos, methamidophos, Metharhizium anisopliae, Metharhizium flavoviride, methidathion, methiocarb, methomyl, methoprene, methoxychlor, methoxyfenozide, metofluthrin, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl, Paecilomyces fumosoroseus, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, potassium oleate, prallethrin, profenofos, profluthrin, promecarb, propaphos, propargite, propetamphos, propoxur, prothiofos, prothoate, protrifenbute, pymetrozine, pyraclofos, pyrafluprole, pyresmethrin, pyrethrum, pyridaben, pyridalyl, pyridaphenthion, pyridathion, pyrimidifen, pyriprole, pyriproxyfen, quinalphos, resmethrin, RH-5849, ribavirin, RU-12457, RU-15525, rynaxapyr, S-421, S-1833, salithion, sebufos, SI-0009, silafluofen, spinosad, spirodiclofen, spiromesifen, sulfluramid, sulfotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogenoxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, triflumuron, trimethacarb, vamidothion, vaniliprole, verbutin, Verticillium lecanii, WL-108477, WL-40027, yl-5201, yl-5301, yl-5302, XMC, xylylcarb, ZA-3274, zeta-cypermethrin, zolaprofos, ZXI-8901, the compound 3-methylphenyl propylcarbamate (Tsumacide Z), the compound 3-(5-chloro-3-pyridinyl)-8-(2,2,2-trifluoroethyl)-8-azabicyclo[3-.2.1]octane-3-carbonitrile (CAS-Reg. No. 185982-80-3) and the corresponding 3-endo-isomer (CAS-Reg. No. 185984-60-5) (cf. WO-96/37494, WO-98/25923), and also preparations which comprise insecticidally active plant extracts, nematodes, fungi or viruses.

As used herein, all numerical values relating to amounts, weight percentages and the like are defined as "about" or "approximately" each particular value, namely, plus or minus 10% (±10%). For example, the phrase "at least 5% by weight" is to be understood as "at least 4.5% to 5.5% by weight." Therefore, amounts within 10% of the claimed values are encompassed by the scope of the claims.

The percentages of the components in the formulations are listed by weight percentage.

The following examples are intended to illustrate the present invention and to teach one of ordinary skill in the art how to make the formulations of the invention. They are not intended to be limiting in any way.

EXAMPLES

Preparation of Low VOC Formulations

Before preparing the formulations, the amount of the components must be calculated (see tables below). Applicants used $GA_3$, $GA_4$, and $GA_{4/7}$ in the form of Technical Grade Active Ingredient ("TGAI") when preparing formulations of the present invention. The percent $GA_3$, $GA_4$, and $GA_{4/7}$ in the technical grade typically ranged between 85% w/w to 96.6% w/w. Variations in the activity of $GA_3$, $GA_4$, and $GA_{4/7}$ in the TGAI should be accounted for by decreasing or increasing the amount of diluent in producing the desired percent of $GA_3$, $GA_4$, and/or $GA_{4/7}$ formulation. This is standard practice within the guidelines of US Environmental Protection Agency per 40 C.F.R. §158.175(b)(2).

Example 1

Preparation of a Low VOC 4% Gibberellic Acid Formulation

TABLE 1

| Raw Material | % wt/wt | g/batch |
| --- | --- | --- |
| PEG 200 | 95.13 | 1426.95 |
| $GA_3$ TGAI, 90% purity | 4.67 | 70.05 |
| Polysorbate 20 (Tween ® 20) | 0.20 | 3.00 |
| Total | 100 | 1500.0 |

As shown in Table 1, 1426.95 grams of PEG 200 was initially warmed (21.2° C.). The polysorbate 20 was added while mixing and mixed for 6 minutes (Temp. 29° C.). The heat source was removed and the $GA_3$ was charged under stirring. The mixing was continued for 60 minutes and the formulation was allowed to cool prior to packaging. A clear solution was obtained which had a pH of 3.02 and contained 4.08% wt/wt $GA_3$.

Example 2

Preparation of a Low VOC 5.8% Gibberellic Acid Formulation

TABLE 2

| Raw Material | % wt/wt | g/batch |
| --- | --- | --- |
| PEG 200 | 93.14 | 1397.10 |
| $GA_3$ TGAI, 90% purity | 6.46 | 96.90 |
| Polysorbate 20 (Tween ® 20) | 0.40 | 6.00 |
|  | 100 | 1500.0 |

As shown in Table 2, 1397.10 grams of PEG 200 was charged in a 2-liter glass beaker and heated to 43° C. The polysorbate 20 was charged and allowed to mix for 3 minutes. The $GA_3$ was then added while mixing. The contents were allowed to cool and packaged. The formulation contained 5.85% wt/wt $GA_3$ and had a pH of 2.95.

Example 3

Preparation of a Low VOC 2.9% Gibberellic Acid Formulation

TABLE 3

| Raw Material | % wt/wt | g/batch |
| --- | --- | --- |
| PEG 200 | 96.58 | 1448.7 |
| GA$_3$ TGAI, 90% purity | 3.22 | 48.3 |
| Polysorbate 20 (Tween ® 20) | 0.20 | 3.00 |
| Total | 100 | 1500.0 |

As shown in Table 3, 1448.7 grams of PEG 200 was charged in a 2-liter glass beaker. The polysorbate 20 was added while mixing and warming to 30° C. The GA$_3$ was added and mixed for 80 minutes. A clear white solution was obtained and packaged. The formulation contained 2.88% wt/wt GA$_3$ and had a pH of 3.12.

Example 4

Preparation of a Low VOC 5.8% Gibberellic Acid Formulation

TABLE 4

| Raw Material | % wt/wt | Kg/batch |
| --- | --- | --- |
| PEG 200 | 93.59 | 33.700 |
| GA$_3$ TGAI, 96.6% purity | 6.01 | 2.164 |
| Polysorbate 20 (Tween ® 20) | 0.40 | 0.144 |
| Total | 100.0 | 33.008 |

As shown in Table 4, a large batch was formulated. 33.7 Kg of PEG 200 was pre-warmed to 37° C. The polysorbate 20 was added while mixing. The GA$_3$ was slowly charged over a 6 minute period and continually mixed for 60 minutes. The clear solution was allowed to cool and packaged. The formulation contained 5.82% wt/wt GA$_3$ and had a pH of 2.85.

Stability Tests

Example 5

Formulations were prepared with different solvents using procedures similar to those described in the above Examples. In each formulation, as illustrated in Table 5 below, the amount of GA$_3$ (5.95%) and polysorbate surfactant (0.40%) remained constant. The type of surfactant remained constant, as well. Further, the amount of solvent remained the same at 93.65%. In Formulation A, PEG 300 was used. In Formulation D, PEG 400 was used. In Formulation D, triethyl citrate was used. The results can be seen below in Table 5.

TABLE 5

| No. | RAW MATERIAL | Form. A g/batch | Form. D g/batch | Form. B g/batch |
| --- | --- | --- | --- | --- |
| 1 | GA3 TGAI 0.976 Purity | 5.95 | 5.95 | 5.95 |
| 2 | Tween ® 20 Polysorbate 20 | 0.40 | 0.40 | 0.40 |
| 3 | Canapeg 300 PEG 300 | 93.65 | — | — |
| 4 | PEG 400 | — | 93.65 | — |
| 5 | Citroflex 2 Triethyl citrate | — | — | 93.65 |
| | Total | 100.0 | 100.0 | 100.0 |
| | Observation | Soluble/ Clear Solution | Soluble/ Clear Solution | Not soluble/ Forms suspension |
| | Freezer Stability | Solidified | Solidified | — |

The stability tests were performed as follows. The solvent was charged in a 150 mL glass beaker containing a magnetic stir bar. The solvent was warmed on a hot plate while stirring. The polysorbate surfactant was charged when the solvent temperature reached 30 to 38 degrees Celsius. The formulations were mixed until they were solubilized (1 to 4 minutes). Then the GA$_3$ TGAI was added under stirring and the temperature was raised to 38 to 41 degrees Celsius. The heat was discontinued and the formulations were mixed for 30 to 50 minutes. The formulations were then observed for solubility. Next, the formulations were packaged, labeled and subjected to freezing temperatures. The formulations were then observed for cold temperature stability.

Formulations A and D, with polyethylene glycol 300 and polyethylene glycol 400, provided clear solutions. The GA$_3$ was soluble in both of these Formulations. However, Formulation B did not form a solution. Instead, Formulation B formed an undesirable suspension and the GA$_3$ was not soluble. Accordingly, Applicants determined that triethyl citrate was not compatible as a solvent in the formulations of the present invention. Applicants found that PEG 300 and PEG 400 were satisfactory for use in the formulations of the present invention.

Formulations A and D solidified during freezer storage. Freezing under cold temperatures is an undesirable characteristic of agricultural formulations, but PEG 300 and PEG 400 could still be used in formulation of the present invention because they formed soluble clear solutions.

Example 6

The formulations were prepared with different solvents using procedures similar to those described in the above Examples. Like Example 5, the type of polysorbate surfactant remained constant in all of the formulations. In this test, Formulation C contained Jeffersol AG-1555 Carbonate and Formulation E contained glycerol. These formulations were compared to Formulations F and G that contained PEG 200. Jeffersol AG-1555 Carbonate is a proprietary solvent for use in formulations. Stability tests were conducted as indicated in Example 5. The results can be seen below in Table 6.

TABLE 6

| No. | RAW MATERIAL | Form. C g/batch | Form. E g/batch | Form. F g/batch | Form. G g/batch |
| --- | --- | --- | --- | --- | --- |
| 1 | GA3 TGAI 0.976 Purity | 5.95 | 5.95 | 8.93 | 12.03 |
| 2 | Tween ® 20 Polysorbate 20 | 0.40 | 0.40 | 0.60 | 0.80 |

TABLE 6-continued

| No. | RAW MATERIAL | Form. C g/batch | Form. E g/batch | Form. F g/batch | Form. G g/batch |
|---|---|---|---|---|---|
| 3 | Jeffsol AG-1555 | 93.65 | — | — | — |
| 4 | Glycerol | — | 93.65 | — | — |
| 5 | PEG 200 | — | — | 90.47 | — |
| 6 | PEG 200 | — | — | — | 87.17 |
| | Total | 100.0 | 100.0 | 100.0 | |
| | Observation | Insoluble Suspension | Insoluble Suspension | Clear Solution | Mostly Soluble, Slight Precipitate |
| | Freezer Stability | | | Liquid | |

Formulations C and E provided insoluble suspensions and Applicants determined that these solvents were incompatible with the formulations of the present invention. Formulations F and G provided more desirable solutions. Formulation F was also liquid under cold temperature conditions.

Formulations F and G also performed better even though they had much higher levels of $GA_3$ (8.93 and 12.03, respectively) than formulations C and E. Accordingly, it was determined PEG 200 was a superior solvent in formulations of the present invention.

Example 7

In this stability study, a formulation was made using procedures similar to those described in the above Examples. This formulation, Formulation H, contained Canapeg 300, which is a PEG 300. The stability testing was conducted as indicated in Example 5, except freezer stability was not determined. The results of this study can be seen below in Table 7.

TABLE 7

| No. | RAW MATERIAL | Form. H g/batch |
|---|---|---|
| 1 | $GA_3$ TGAI 0.976 Purity | 12.03 |
| 2 | Tween ® 20 | 0.80 |
| 3 | Canapeg 300 PEG 300 | 87.17 |
| | Total | 100.0 |
| | Observation | Partial Solubility/Cloudy |

Formulation H provided a cloudy and a partially soluble solution in a formulation with a high amount of $GA_3$ (over 12%).

Example 8

In this stability study, a formulation was made using procedures similar to those described in the above Examples. These formulations contained $GA_4$ or $GA_{4/7}$. The stability testing was conducted as indicated in Example 5. The results of this study can be seen below in Table 8.

TABLE 8

| No. | RAW MATERIAL | Form. I g/batch | Form. J g/batch |
|---|---|---|---|
| 1 | $GA_{4/7}$ TGAI 0.90 Purity | — | 6.45 |
| 2 | $GA_4$ TGAI 0.90 Purity | 6.45 | — |
| 3 | PEG 200 | 93.15 | 93.15 |
| 4 | Tween ® 20 (Polysorbate 20) | 0.40 | 0.40 |
| | Total | 100.0 | 100.0 |
| | Solvent Temp, ° C. (Prior to Tween ® 20) | 35 | 30 |
| | Tween ® 20 Mix time (Min.) | 1 | 1 |
| | Temp. Prior to Gibb Addition; ° C. | 36 | 38 |
| | Final Mix Time (Min.) | 30 | 30 |
| | Observation | Soluble @ 15 Minutes | Soluble @ 15 Minutes |
| | Yield, g | 99.2 | 99.1 |

Applicants found that Formulations I and J, with 5.8% of $GA_4$ and $GA_{4/7}$ respectively, provided clear solutions illustrating that $GA_4$ and $GA_{4/7}$ are completely soluble in polyethylene glycol.

The stability tests provided herein illustrate the difficulty one of skill in the art encounters when attempting to create formulations with all of the desirable, and commercially important, qualities. Applicants found that many different solvents were not compatible, however, they found that PEG 200, PEG 300 and PEG 400, provided satisfactory results in the formulations.

Example 9

In this study, Applicants compared formulations of the present invention with successful, commercially available formulations. Specifically, Applicants compared formulations of the present invention containing 5.8% and 2.9% $GA_3$ with the standard ProGibb® 4% solution formulation and ProGibb® 40% water-soluble granular formulation to determine their effects on the berry size of table grapes.

Applicants applied the treatments to Thompson Seedless grape vines growing on a gabled trellis system in California. The vineyard was established seven years before this study began. The study was a randomized complete block design, with each treatment consisting of 8 replicates of 1 vine each. There were 519 vines per acre and the crop loads were manually thinned to 45 to 50 clusters per vine.

The treatments were applied at the rate of 44 grams per active ingredient per acre with a backpack mist blower. The initial treatment was made when the berries were 4 to 5 mm in size. The second treatment occurred about 2 weeks later when the berries were 10 to 11 mm in size. The treatments were applied at 200 gallons per acre to ensure coverage of the clusters. A surfactant was included at a rate of 0.031% v/v.

At harvest, the number of berries per cluster, weight per berry, rachis weight, stem length and soluble solids were determined. Soluble solids were determined from a macerated composite sample from all of the sampled berries from an individual replicate.

The results of this study are below in Table 9.

TABLE 9

| Test | ProGibb ® 4% g/batch | ProGibb ® 40% g/batch | 5.8% Form. g/batch | 2.9% Form. g/batch |
|---|---|---|---|---|
| Berries per shoulder (number) | 31 | 26 | 30 | 30 |
| Weight/Shoulder (gm) | 148.2 | 108.3 | 145.3 | 146.6 |
| Weight/Berry (gm) | 4.9 | 4.6 | 4.7 | 4.8 |
| Rachis Weight (gm) | 3.8 | 3.2 | 3.5 | 3.7 |
| Rachis Length (cm) | 9.6 | 9.3 | 10.1 | 9.4 |
| Soluble Solids (Brix) | 16.0 | 16.2 | 15.9 | 16.7 |

Example 10

In this study, Applicants again compared the formulations of the present invention with commercial $GA_3$ formulations. This Thompson Seedless table grape vineyard in California was established thirty years before the study began. The study had the same design as Example 9. The results are below in Table 10.

TABLE 10

| Test | ProGibb ® 4% g/batch | ProGibb ® 40% g/batch | 5.8% Form. g/batch | 2.9% Form. g/batch |
|---|---|---|---|---|
| Berries per shoulder (number) | 31 | 26 | 27 | 25 |
| Weight/Shoulder (gm) | 152.9 | 144.5 | 146.3 | 131.5 |
| Weight/Berry (gm) | 5.2 | 5.9 | 5.9 | 5.7 |
| Rachis Weight (gm) | 3.8 | 3.8 | 3.5 | 3.2 |
| Rachis Length (cm) | 9.3 | 9.1 | 8.5 | 8.9 |
| Soluble Solids (Brix) | 17.0 | 16.5 | 16.8 | 16.4 |

Example 11

In this study, Applicants again compared the formulations of the present invention with commercial $GA_3$ formulations. This Flame Seedless table grape vineyard in California was established seven years before the study. The study had the same design as Example 9 except that the first treatment was applied when the berries were 7 to 8 mm in size and the berries were 11 to 13 mm when the second treatment was applied. The results are below in Table 11.

TABLE 11

| Test | ProGibb ® 4% g/batch | ProGibb ® 40% g/batch | 5.8% Form. g/batch | 2.9% Form. g/batch |
|---|---|---|---|---|
| Berries per shoulder (number) | 24 | 22 | 24 | 24 |
| Weight/Shoulder (gm) | 138.1 | 128.2 | 128.5 | 127.6 |
| Weight/Berry (gm) | 5.7 | 5.9 | 5.4 | 5.3 |
| Rachis Weight (gm) | 2.9 | 2.8 | 2.6 | 2.7 |
| Rachis Length (cm) | 7.7 | 8.0 | 7.6 | 7.6 |
| Soluble Solids (Brix) | 14.9 | 14.8 | 14.9 | 15.1 |

Example 12

In this study, Applicants again compared the formulations of the present invention with commercial $GA_3$ formulations. This Flame Seedless table grape vineyard in California was established seven years before the study. The study had the same design as Example 11. The results are below in Table 12.

TABLE 12

| Test | ProGibb ® 4% g/batch | ProGibb ® 40% g/batch | 5.8% Form. g/batch | 2.90% Form. g/batch |
|---|---|---|---|---|
| Berries per shoulder (number) | 24 | 22 | 23 | 24 |
| Weight/Shoulder (gm) | 135.3 | 127.3 | 128.5 | 139.1 |
| Weight/Berry (gm) | 5.6 | 5.8 | 5.5 | 5.8 |
| Rachis Weight (gm) | 2.8 | 2.5 | 2.6 | 3.0 |
| Rachis Length (cm) | 7.9 | 7.6 | 8.2 | 8.4 |
| Soluble Solids (Brix) | 15.1 | 14.8 | 15.1 | 15.1 |

To summarize the results of Examples 9 to 12, Applicants found that the formulations of the present invention performed comparably to commercially available formulations. In addition, Applicants found that none of the formulations caused the adverse effects of berry softening, berry shrivel, or phytotoxicity commonly seen with thinning treatments.

We claim:

1. A liquid agricultural formulation consisting of from about 1 to about 10% of at least one gibberellin selected from the group consisting of gibberellic acid ($GA_3$), gibberellin 4 ($GA_4$), and gibberellin $_{4/7}$ ($GA_{4/7}$), from about 85 to about 99% polyethylene glycol with an average molecular weight from about 190 to about 420 and from about 0.1 to about 5% of a non-ionic or anionic surfactant, wherein the percentages are percent by weight of the formulation.

2. The formulation of claim 1 wherein the gibberellin is $GA_3$.

3. The formulation of claim 1 wherein the gibberellin is $GA_4$.

4. The formulation of claim 1 wherein the gibberellin is $GA_{4/7}$.

5. The formulation of claim 1 wherein the non-ionic or anionic surfactant is a polysorbate surfactant.

6. The formulation of claim 5 wherein the polysorbate surfactant is a polysorbate with 20 moles of ethylene oxide per mole of sorbitol.

7. The formulation of claim 2 consisting of from about 2 to about 9% $GA_3$, from about 88 to about 98% polyethylene glycol with an average molecular weight from about 190 to about 420, and from about 0.1 to about 2% of the non-ionic or anionic surfactant.

8. The formulation of claim 2 consisting of from about 4.2 to about 7% $GA_3$, from about 89 to about 97% polyethylene glycol with an average molecular weight from about 190 to about 420, and from about 0.3 to about 0.5% of the non-ionic or anionic surfactant.

9. The formulation of claim 2 consisting of from about 5.4 to about 6% $GA_3$, from about 90.5 to about 96% polyethylene glycol with an average molecular weight from about 190 to about 420, and from about 0.3 to about 0.5% of the non-ionic or anionic surfactant.

10. The formulation of claim 2 consisting of about 5.9% $GA_3$, about 93% polyethylene glycol with an average molecular weight from about 190 to about 420, and about 0.4% of the non-ionic or anionic surfactant.

11. A liquid agricultural formulation consisting of from about 1 to about 10% of at least one gibberellin selected from the group consisting of gibberellic acid ($GA_3$), gibberellin $_4$ ($GA_4$), and gibberellin $_{4/7}$ ($GA_{4/7}$), from about 85 to about 99% polyethylene glycol with an average molecular weight from about 190 to about 210, and from about 0.1 to about 5% of a non-ionic or anionic surfactant, wherein the percentages are percent by weight of the formulation.

12. The formulation of claim 1 consisting of from about 4.2 to about 7% $GA_3$, $GA_4$, $GA_{4/7}$, or combinations thereof, from about 89 to about 97% polyethylene glycol with an average molecular weight from about 190 to about 420, and from about 0.3 to about 0.5% of the non-ionic or anionic surfactant.

13. The formulation of claim 1 consisting of from about 5.4 to about 6% $GA_3$, $GA_4$, $GA_{4/7}$, or combinations thereof, from about 90.5 to about 96% polyethylene glycol with an average molecular weight from about 190 to about 420, and from about 0.3 to about 0.5% of the non-ionic or anionic surfactant.

14. The formulation of claim 1 consisting of about 5.7% $GA_3$, $GA_4$, $GA_{4/7}$, or combinations thereof, about 93.3% polyethylene glycol with an average molecular weight from about 190 to about 420, and about 0.4% of the non-ionic or anionic surfactant.

15. The formulation of claim 11 wherein the gibberellin is $GA_3$.

16. The formulation of claim 11 wherein the gibberellin is $GA_4$.

17. The formulation of claim 11 wherein the gibberellin is $GA_{4/7}$.

18. A method of regulating plant growth comprising the step of treating a seed, soil or a plant with an effective amount of the formulation of claim 1.

* * * * *